(12) United States Patent
Lawitschka et al.

(10) Patent No.: US 10,130,446 B2
(45) Date of Patent: Nov. 20, 2018

(54) DETERMINING POSITION AND ORIENTATION OF A DENTAL IMPLANT

(71) Applicant: Straumann Holding AG, Basel (CH)

(72) Inventors: Uwe Lawitschka, Basel (CH); Frank Homann, Basel (CH); Benjamin Straub, Basel (CH)

(73) Assignee: Straumann Holding AG, Basel (CH)

( * ) Notice: Subject to any disclaimer, the term of this patent is extended or adjusted under 35 U.S.C. 154(b) by 359 days.

(21) Appl. No.: 15/184,062

(22) Filed: Jun. 16, 2016

(65) Prior Publication Data

US 2016/0296301 A1    Oct. 13, 2016
US 2017/0354483 A9    Dec. 14, 2017

Related U.S. Application Data

(63) Continuation of application No. 13/201,142, filed as application No. PCT/EP2010/000854 on Feb. 11, 2010.

(30) Foreign Application Priority Data

Feb. 12, 2009 (EP) .................................... 09001983

(51) Int. Cl.
 G06F 17/50      (2006.01)
 A61C 8/00       (2006.01)
 A61C 9/00       (2006.01)
 A61C 13/34      (2006.01)
 A61C 13/00      (2006.01)

(52) U.S. Cl.
 CPC .......... *A61C 8/0001* (2013.01); *A61C 9/0053* (2013.01); *A61C 13/0004* (2013.01); *A61C 13/34* (2013.01)

(58) Field of Classification Search
 CPC combination set(s) only.
 See application file for complete search history.

*Primary Examiner* — Aniss Chad
*Assistant Examiner* — Cuong V Luu
(74) *Attorney, Agent, or Firm* — Polsinelli, PC

(57) ABSTRACT

Method for determining a position and an orientation of a dental implant includes scanning a surface of a scan body connected to the implant wherein a plurality of data points is determined which correspond to positions of points that are located on the surface of the scan body. The method further included reconstructing at least three planes based on the data points, reconstructing intersection information of the reconstructed planes, where the intersection information includes the reconstruction of straight intersection lines and of intersection points, and determining the position and the orientation of the implant based on the reconstructed intersection information.

7 Claims, 3 Drawing Sheets

DETERMINING POSITION AND ORIENTATION OF A DENTAL IMPLANT

FIELD OF THE INVENTION

The invention concerns a method, which can be executed by a computing device and/or can be stored in the form of computer executable instructions on a computer-readable medium, for determining a position and an orientation of a dental implant. Further, the invention concerns a scan body for determining a position and an orientation of a dental implant.

BACKGROUND

In the field of artificial tooth replacements where one tooth or even several teeth have to be replaced, the corresponding dental prosthesis are usually fixed in a patient's mouth via a dental implant which is fixed (e.g. like a screw) in the bone of a patient's jaw. Whereas there is usually plenty of space for placing a dental implant between two neighboring teeth, for instance, the situation is more tricky for the corresponding dental prosthesis. In order to achieve a qualitatively and aesthetically good result, a dental prosthesis has to fit almost perfectly between neighboring teeth on one hand and the connection between the dental prosthesis and the implant has to be very firm on the other hand, which can be achieved if the connection has basically no play. Besides the final location of a dental prosthesis within an oral environment it is also beneficial to ensure that a dental prosthesis can actually be inserted in between two neighboring teeth and, at the same time, can be connected with the implant.

In order to achieve the above-mentioned tasks and requirements, a possible solution is to determine the position and the orientation of a dental implant with respect to neighbouring teeth and the gingiva between these neighbouring teeth with a certain precision. Typically, this determination has to be performed in a situation, where the implant is not directly visible (e.g. the implant is below the upper edge of the gingiva).

In the prior art, the position and orientation of a dental implant is determined by attaching a scan body to the implant, determining the position and orientation of the scan body (e.g. with an optical scanning method), and determining the position and orientation of the implant relative to the position and orientation of the scan body. In some cases, the scanning procedure is carried out with help of a model which represents the situation of a patient's mouth or in other cases, the procedure is carried out directly in a patient's mouth. In the state of the art, various types of scan bodies with different geometrical properties are used. Once the positions and orientations of a scan body are known, this information is used to obtain the orientation and position of said implant. Whereas dental implants and scan bodies can be produced with high precision, the above-mentioned scanning procedure can be less precise, particularly in situations where distinctive parts, such as corners or edges, of a scan body are only partly visible.

SUMMARY OF THE INVENTION

Therefore, a problem to be solved by the present invention is to determine the position and orientation of a dental implant with a high precision. At the same time, it is desirable that the scanning procedure is relatively simple, especially in case the scanning is performed directly in a patient's mouth where a long-lasting scanning procedure should be avoided.

The method for determining a position and an orientation of a dental implant in one embodiment is a combination of a scanning procedure and a reconstruction procedure. During the scanning procedure, the surface of a scan body which is connected to an implant is scanned by determining a plurality of data points which correspond to positions of points that are located on the surface of the scan body. In another embodiment an already existing data set, having a plurality of data points corresponding to positions of points that are located on the surface of a scan body, is loaded in order to perform the reconstruction of a position and an orientation of a dental implant. Such a data set can be obtained by a scanning method as is mentioned above or below. During the reconstruction phase, these data points are used for reconstructing at least three planes. From the reconstructed planes, intersection information is determined. The intersection information comprises straight intersection lines where at least two planes intersect each other and/or intersection points where at least three planes intersect each other or where a straight intersection line intersects a plane or where at least two straight intersection lines intersect each other. Using the above-mentioned reconstructed intersection information, the position and orientation of the implant can be determined. This determination can be based only on part of the reconstructed intersection information or it can be based on all available reconstructed intersection information which allows an even higher precision since the position and orientation of the implant is over-constrained. In a preferred embodiment an intersection point is reconstructed directly from the at least three reconstructed planes.

It is noted that the scanning points on the surface of the scan body do not necessarily have to correspond to corners or edges. Any point within a planar area can be used for the above-mentioned reconstruction procedure which simplifies the scanning procedure (e.g. scanning of a relatively moderate number of points is sufficient). Preferably, only those points are used for the reconstruction of planes that lie completely inside the corresponding area (i.e. the points, used for the reconstruction of planes, are not located at the corners or edges of the scan body). For the determination of the position and orientation of a dental implant only a minimum of nine points have to be scanned. Typically, more than nine points are scanned, for instance between twenty and one hundred points, in order to make sure that there is a sufficient number of good quality points available for the reconstruction phase. In principle, there is no upper limit of scanning points. The time to perform a scan, however, increases with an increasing number of points. Therefore, the number of scanning points should be less than ten thousand or even less than one thousand.

In a preferred embodiment, the determination of the position and orientation of the implant comprises associating reconstructed geometrical elements with physical geometrical elements of the scan body. For instance, reconstructed planes can be associated with physical plane areas of the surface of the scan body. Alternatively, or in addition, reconstructed straight intersection lines can be associated with physical edges of the scan body and/or reconstructed intersection points can be associated with physical corners of the scan body. It is noted that physical corners (and also edges) are not perfect corners in a mathematical sense, but are rounded corners (or edges) with a bending radius that is typically less than 0.05 mm. It should be understood that the reconstructed geometrical objects correspond to physical geometrical objects of a part of the scan body that actually has been scanned.

In order to be able to determine the position and an orientation of the implant, a minimum of information is required. One possibility is to reconstruct the position and orientation of the implant using one reconstructed intersection point and one reconstructed straight intersection line and/or two reconstructed intersection points and/or two reconstructed straight intersection lines which intersect each other. Further, it is possible to determine the position of the implant based on the above-mentioned minimum information plus additional information or to determine the implant position directly based on at least, three reconstructed planes. Preferably, the reconstruction of planes from the data points is performed based on a sub-set of data points. In case there are only three data points available, a corresponding plane is simply calculated. However, in case there are more than three points available for reconstructing a plane, it is possible to fit a plane through the data points. For this purpose, a standard fitting procedure can be used (e.g. a $\chi^2$ based fitting procedure). Further, the determination of the position and the orientation of the implant is typically based on information regarding the dimensions of the scan body and/or the implant and/or other parts in between the scan body and the implant in addition to the reconstructed geometrical information. Such a part which is located between the scan body and the implant is, for instance, an adaptor piece, which allows to use the same scan body with different types of implants. Further, an adaptor piece can be used to adjust the height of the scan body (e.g. in case the top of the scan body is too far below the occlusal plane), or in some cases, an adaptor piece is useful to adapt the angle of the scan body with respect to the implant (e.g. in case the implant orientation is considerably off vertical).

In another embodiment of the present invention, the method for determining a position and orientation of a dental implant, further comprises the generation of a digital/virtual model of at least a part of the implant inside the mouth of a patient. The digital/virtual model is preferably three-dimensional so that the model can be viewed from different angles which is useful to study the insertion of a dental prosthesis, for instance. The digital/virtual model can further reflect information about neighbouring teeth and the gingiva in the neighbourhood of the implant if this information is available (e.g. also determined during the scanning procedure or obtained from some kind of database).

Typically, the scanning procedure is performed on a physical model which has been made by a dentist and a dental technician, respectively, and which reflects the situation in a patient's mouth and comprises an implant analog which corresponds to an implant in a patient's mouth. Usually, only the relevant part of the patient's mouth is modelled. Making use of a physical model allows testing the insertion procedure of a dental prosthesis, for instance, or allows performing of the scanning in a dental laboratory where a patient is not required to be available. Alternatively, the scanning procedure can be performed directly in a patient's mouth where the implant is already fixed in the bone of a patient's jaw and the scan body is attached to the implant.

The invention further concerns a computing device that is capable of performing the above-mentioned method steps. For this purpose, a scanning device is typically connected to the computing device and the scan data (e.g. data points) are directly transferred to the computing device. However, it is also possible to render the scanning information in a different way such as using an IR transmission, a telecommunication system or transferring the data with the help of a data storage means. Further, the invention concerns a computer-readable medium having stored thereon, computer executable instructions for performing the above-mentioned method steps when said instructions are executed. Furthermore, there is the possibility that the computing device and/or computer readable medium is part of a scanning device.

Another aspect of the invention is related to a scan body for determining the position and orientation of a dental implant. The scan body has a bottom end that allows connecting the scan body with an implant where the scan body is typically connected to the implant via an adaptor piece but there are other embodiments where a scan body is connected directly with an implant. Further, the scan body has a top end with a scan geometry that is scanned during the scanning procedure. The scan geometry is characterized in that its surface comprises a plurality of plane areas where at least some of said plane areas have to be partly visible during the scanning procedure. This means that from every possible point of view, at least three plane areas have to be at least partly visible. In case the top end of the scan body points upwards and the bottom end of the scan body points downwards, a possible point of view is either located above the scan body or at the same level (beside) of said scan geometry. The idea of these visibility requirements is to ensure that at least three plane areas are at least partly visible from any point above the level of the scan geometry or at the same level of the scan geometry because the scan information of these at least three plane areas is used to reconstruct at least three planes which are needed in one embodiment for determining the position and orientation of a corresponding dental implant which is connected to the scan body. Requiring the possibility that at least three planes of the scan geometry are visible from the side is in particular useful in cases when the location of the implant is determined with respect to neighbouring teeth from the opposite side jaw of a patient (e.g. when the teeth of the upper jaw and the teeth of the lower jaw touch each other, to ensure that a patient will be able to properly bite with a new dental prosthesis).

There are various types of scan geometries thinkable which are typically polyhedral. The overall shape of a scan body is approximately cylindrical where the longitudinal axis of the scan body connects the center of the top end with the center of the bottom end of the scan body. Since a plurality of plane areas are required to be visible from different angles with respect to longitudinal axis of the scan body, in a preferred embodiment of the invention at least two of the at least three visible plane areas are required to have a different angular orientation with respect to the longitudinal axis, preferably there are even at least three types of plane areas with different orientation angles. Advantageously, the orientation angle with respect to the longitudinal axis of at least one type of plane area lies within the range of 30° to 60° or 40° to 50°. Further, there is preferably one type of plane area that is perpendicular to the longitudinal axis of the scan body and/or there is preferably one type of plane area that is parallel to the longitudinal axis of the scan body. In a further embodiment, it is required that there are at least two or three types of plane areas with different numbers of corners and/or a different number of sides and/or sides with different lengths, respectively. In another preferred embodiment, the scan geometry comprises at least four visible corners such that three of said four visible corners lie within a plane and one of said four corners lies outside said plane. The requirements regarding the number of types of plane areas having different features and/or the number of visible corners in a certain constellation help to ensure that the at least three required plane areas are easily visible from every possible point of view. Further, the above-mentioned requirements lead to scan geometries with a number of planes that is typically above eight or fifteen and/or a number of corners that is typically above five or eleven, respectively. In principle, there is no upper limit in the number of planes and corners respectively. In case the number of planes/corners is large, however, the size of individual planes will in turn become small, which can lead to a more complex scanning procedure. Therefore, an upper limit of twenty, thirty, fifty or one hundred plane areas and/or thirty or fifty corners, respectively, is desirable. Further, the scan geometry comprises different types of plane areas with different shapes, such as triangles and/or squares and/or pentagons and/or more complex shapes.

In another embodiment of the invention, a scan body comprises a coding associating the scan body with a particular type of implant and/or with a particular type of adaptor piece. For this purpose, typically, ribs and/or channels and/or coloured rings are located just below the scan geometry. The coding or the area where a coding would be expected, has to be visible from every possible point of view during the scanning procedure, where a possible point of view is defined correspondingly to a possible point of view regarding the scan geometry with the difference that the coding does not have to be visible from directly above but only sideways above the coding or scan body, respectively. In case the coding is not visible during the scanning procedure, the coding information or the respective identification information can be obtained "manually" (e.g. by a user looking at the coding and looking up the corresponding information that is represented by the coding). Further, the coding can comprise letters and/or numbers and/or other symbols.

The coding may also be part of the adaptor piece and refer to a particular implant which means that by scanning the coding on the adaptor piece the e.g. type or size of the implant can be determined.

In a further embodiment of the present invention, the scan geometry of the scan body is such that some parts of the scan geometry are light reflective and/or some parts of the scan geometry are non-light reflective, for instance, only a part of a plane area is light reflective and the rest of the plane area is non-light reflective (e.g. the inner part of a plane are is light reflective whereas the border area of a plane area is non-light reflective). In this way, it is possible to simplify the recognition of plane areas during the scanning/reconstruction procedure. Alternatively, it maybe sufficient to have different regions with different reflection coefficients in order to allow an easy detection of the plane areas.

The invention also refers to a scan body in combination with a set of adaptor pieces, with which the scan body can be attached to different implants by different adaptor pieces. Preferably each adaptor piece corresponds to a particular implant and for different implants different adaptor pieces are provided. Preferably each adaptor piece is provided with a coding that can be optically scanned, wherein the coding allows to identify the type of implant or the size of the implant which corresponds to the adaptor piece. An adaptor piece is typically fixed on top of an implant with help of a screw or a catcher. If a permanent connection is desired, the adaptor piece can also be glued to the implant.

BRIEF DESCRIPTION OF THE FIGURES

Further aspects of possible embodiments of the invention become clear from FIGS. 1, 2a to 2e and 3a to 3f.

DETAILED DESCRIPTION

Figure 1:
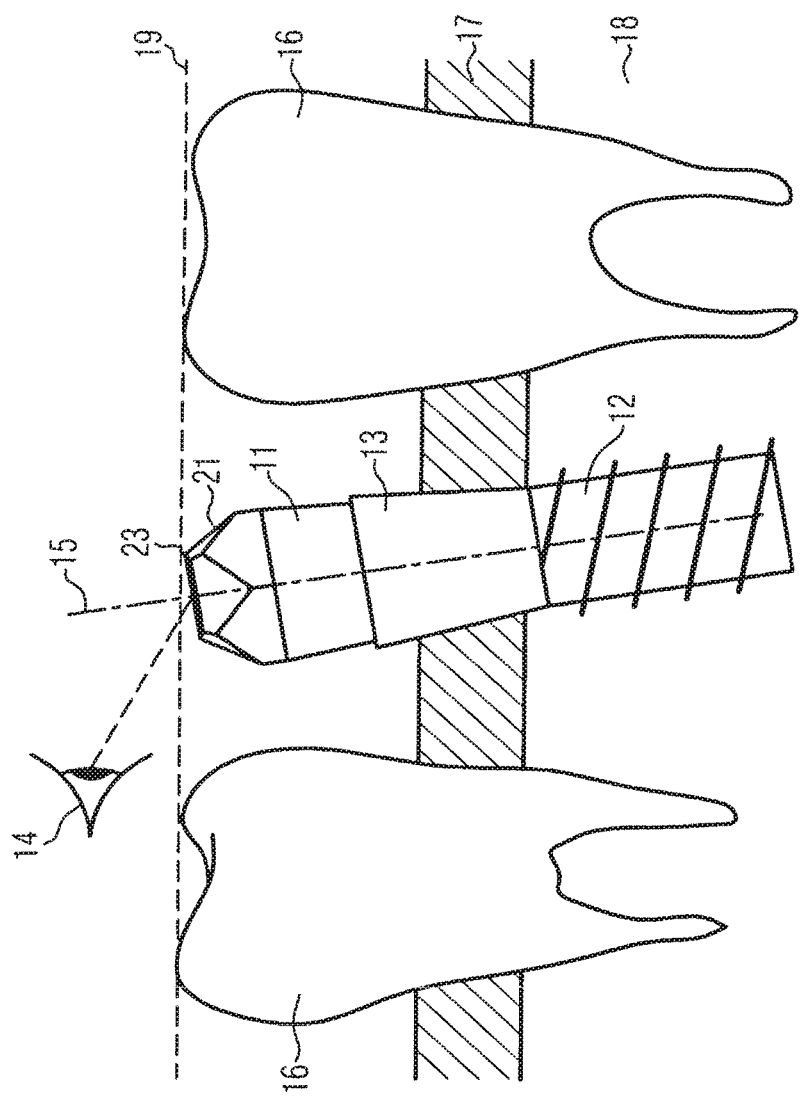
FIG. 1 shows the overall situation when a position and orientation of a dental implant is determined.

In FIG. 1, a possible set-up for determining a position and an orientation of an dental implant 12 is illustrated. The set-up either reflects the situation in the mouth of a patient or reflects the situation in a model of a patient's mouth. An implant 12 is fixed in the bone 18 of a jaw. Above the bone 18 there is layer of gingiva 17. A scan body 11 is attached to the implant 12 via an adaptor piece 13 which is located partly above the level of the gingival 17. To the left and to the right of the scan body 11, two neighbouring teeth 16 are illustrated. However, in some cases, there is only one neighbouring tooth 16 next to the implant 12. It should be noted that the longitudinal axis 15 of the scan body 11 and/or the implant 12 and/or the adaptor piece 13 is not necessarily exactly vertical or is not exactly perpendicular to the surface of the bone 18, respectively. Further, when scanning the scan geometry 21 of the scan body 11, the point of view 14 of the scanning device is not necessarily located exactly above the scan body 11, but the point of view 14 can be located sideways and/or at the side of the scan geometry 21 of the scan body 11. In order to be able to achieve good scanning results, the topmost part 23 of the scan body 11 lies at or just below the level of the occlusal plane 19 which is defined by the height of the neighbouring teeth 16. Typically, the distance between the surface of the bone 18 and the occlusal plane 19 is about 9 mm to 11 mm which means that the scan body 11 should have a length less than these values. If however, the scan body 11 is too short (to low with respect to the occlusal plane 19), it is possible to extend the length by using a suitable adaptor piece 13. On the other hand, if a scan body 11 would be too long (e.g. would lie partly above the occlusal plane 19) then it would likely to be out of the scan corridor, which is adapted to scan teeth or residual tooth portions. The typical size of a scan corridor is 15-20 mm×15-20 mm with a length between 25-50 or 30 to 45 mm. The scan corridor may have a square or rectangular cross section (in a section perpendicular to its length).

The scenario, illustrated in FIG. 1, is only one possibility. There are many other scenarios possible, too. For instance, there could be two teeth missing, which would result in a larger gap in between the two neighbouring teeth 16. The latter scenario would typically comprise two dental implants 12, of which the relative position and orientation of the implants 12 to each other could be determined using two scan bodies 11, where each one would be connected to one of the two implants 12. Other scenarios could comprise three or even more implants 12 and several scan bodies 11, respectively.

Figures 2A, 2B, 2C:
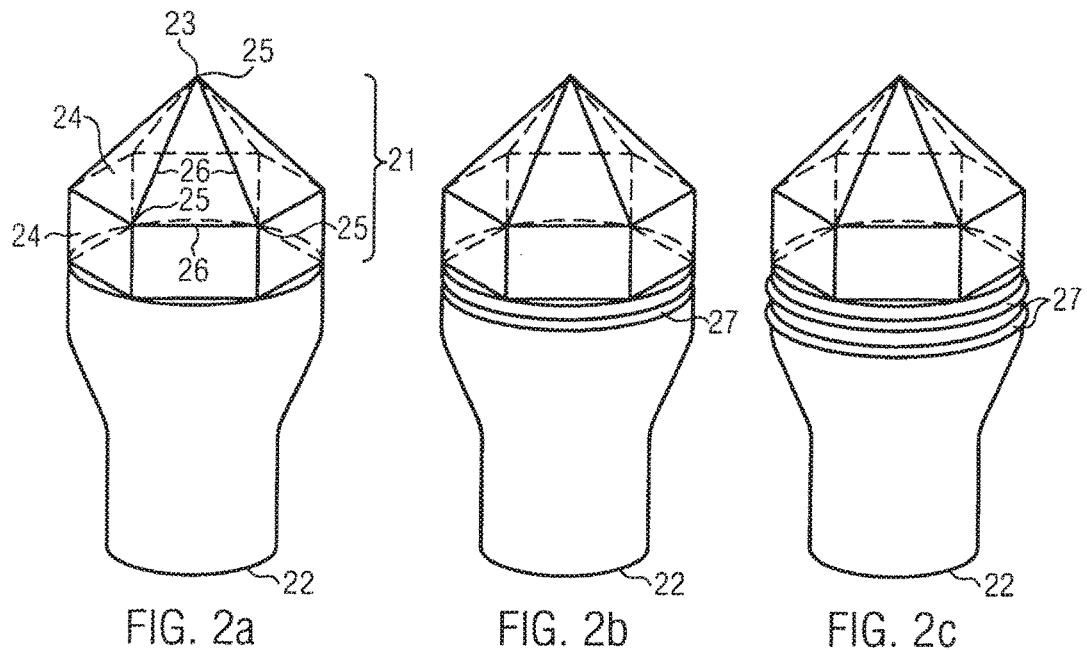
FIGS. 2a to 2e show various embodiments of scan bodies.
Figures 2D, 2E:
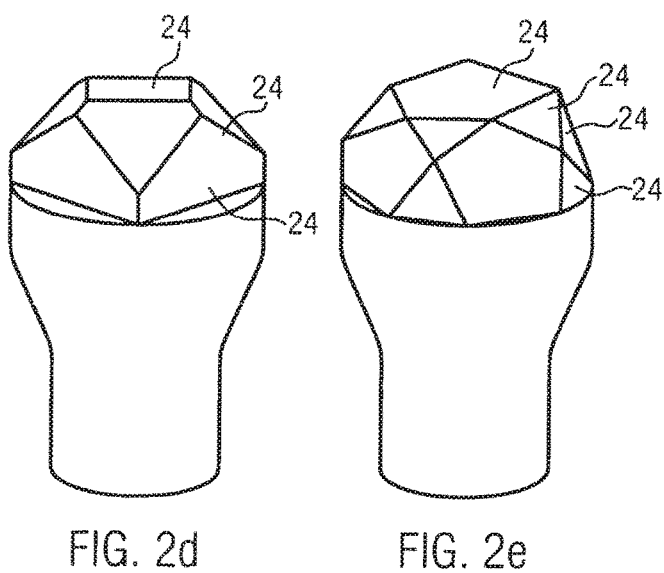

FIGS. 2a through 2e show several embodiments of scan bodies 11, each scan body 11 having a bottom end 22 which can be attached to an implant 12 or an adaptor piece 13, and a top end 23 which comprises a scan geometry 21. The scan geometry 21 comprises several plane areas 24 which have corners 25 and sides 26 where the sides 26 can be also considered as edges 26 of the scan geometry 21. In the particular case of FIG. 2a, the scan geometry 21 consists of six squares and six triangles as plane areas 24. However, there are other types of scan geometries 21 possible, such as is illustrated in FIGS. 2d and 2e, for example. The scan geometry 21 of FIG. 2d consists of three types of plane areas 24, namely, one square plane area 24, four pentagonal areas 24 of a first type and four pentagonal areas 24 of a second type. In case of FIG. 2e, the scan geometry 21 comprises three types of plane areas 24, namely, ten triangles, six pentagons, and one hexagon. In FIGS. 2b and 2c, the scan body 11 of FIG. 2a is shown with additional codings 27 just below the scan geometry 21, but it would be also possible for the coding 27 to be part of the scan geometry 21. In FIG. 2b, the coding 27 is a single channel surrounding the scan body 11 and in case of FIG. 2c, the coding 27 consists of two ribs. As for the scan geometry 21, the coding 27 or the area where one would expect a coding 27 (e.g. in case there is a void coding 27) has to be visible from every possible point of view 14, such that, during the scanning procedure, the scan body 11 can be identified by scanning/recognizing the coding 27.

Figure 3A:
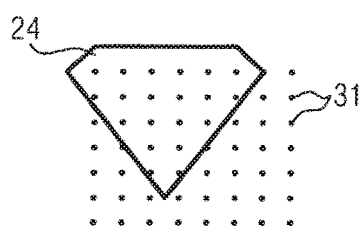
FIGS. 3a to 3f illustrate steps related to the determination of a position and an orientation of a dental implant.
Figure 3B:
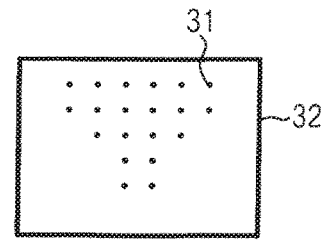
Figure 3C:
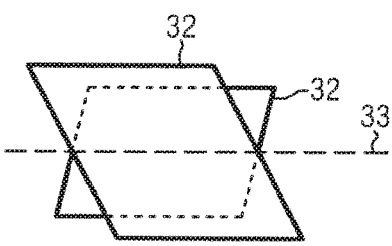
Figure 3D:
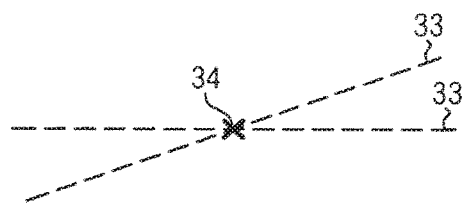
Figure 3E:
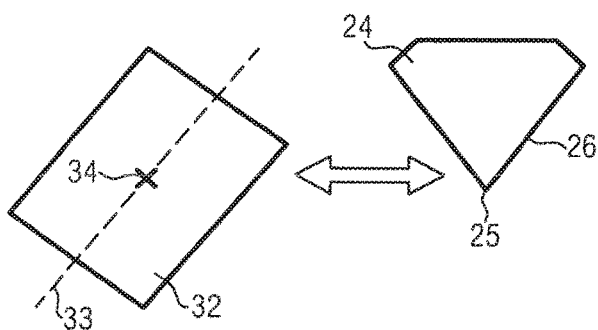
Figure 3F:
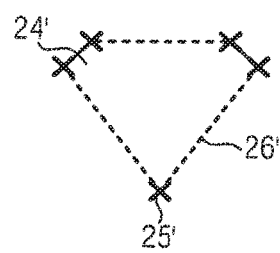

In FIGS. 3a to 3f, several steps of the scanning procedure and data processing are illustrated. FIG. 3a shows an exemplary plane area 24 which is scanned by taking an array of (data) points 31. The points 31 which lie inside the plane area 24 (possibly also including the borders), are used to reconstruct a plane 32. Typically, plane 32 is reconstructed with help of a fitting procedure which can include accepting and rejecting of data points 31 using certain selection criteria (e.g. points 31 which are too far from a first estimate of plane 32 are rejected). If two planes that intersect each other have been reconstructed, a straight intersection line 33 can be determined as is shown in FIG. 3c. Further, in case there are two straight intersection lines 33 which intersect each other, an intersection point 34 can be reconstructed as is illustrated in FIG. 3d. An intersection point 34 can also be determined from the intersection of three, or even four, five or more, planes 32 with those planes 32 corresponding to plane areas 24 neighbouring a corner 25 to which the intersection point 34 corresponds. The latter case does not require the explicit reconstruction of straight intersection lines 33, and therefore the step, illustrated in FIG. 3c, may be omitted. Implicitly, the reconstruction of one intersection point 34, requires at least three reconstructed planes 32 or three plane areas 24, respectively. In FIG. 3e, the correspondence of physical geometrical elements and reconstructed geometrical elements is determined. For instance, intersection point 34 corresponds to corner 25 and part of straight intersection line 33 corresponds to side/edge 26. Further, part of plane 32 corresponds to the physical plane area 24. Using this correspondence information, a digital/virtual model of the plane area 24 can be built. The virtual plane area 24' consists of several virtual corners 25' which correspond to reconstruction intersection points 34 and of several virtual sides 26' which correspond to parts of reconstructed straight intersection lines 33. In this way, it is possible to create a model of the whole scan geometry 21 or even to create a digital/virtual model of the whole scan body 11, the dental implant 12, the adaptor piece 13 and even of part of the patient's mouth, respectively. In the latter case, however, additional scanning information and/or additional stored information (e.g. coming from a database) is necessary.

The procedure, described in context with FIGS. 3a to 3f, can additionally involve one or more optional steps which are described in the following. After a set of points 31 has been obtained by scanning the surface of a scan body 11, the surface of the scan body can be approximately described using finite elements such as triangles, for instance (in the following the example of triangles is used, but in general other finite elements than triangles such as rectangles, quadrangles or other polygons may be equally used). The finite elements can be used to form a mesh (based on the set of points 31) which describes the surface of the scan body. Each triangle has three corners, and the orientation of each triangle is described by a normal vector of the plane in which the triangle lies. In a consequent step, a person/user can explicitly select a plane area 24 of the scan geometry 21 by clicking on a triangle which lies in said plane area 24. This kind of user selection helps to associate a detected plane area with a real plane area 24 of the scan geometry 21. In particular, such a user selection of a plane area 24 is helpful in case said plane area 24 is a single plane area 24 at the top end 23 of the scan geometry 21, as is the case for the scan bodies 11 shown in FIGS. 2d and 2e. In this case the normal vector of said plane area 24 is parallel to the longitudinal axis 15 of the scan body 11. Since this particular type of plane area 24 allows a precise determination of the position of the top end 23 and the orientation of the scan body 11, this plane area 24 helps to determine the position and orientation of a dental implant 12 with a high precision. In addition, the user selection of said particular type of plane area 24 can simplify (and therefore speed up) the determination of position and orientation.

Upon a user selection of a triangle in the further processing preferably only those triangles are used which are within a sphere with a radius between 2 and 3 mm since in this way, neighbouring triangles, which are located inside the sphere, ideally describe the entire surface of the scan geometry 21, which can be taken into account when determining the position and orientation of the corresponding plane area 24, scan body 11 and implant, respectively. More specifically, the (visible) plane areas 24 of the scan geometry 21 can be described by considering all triangles inside the above mentioned sphere and by grouping the triangles according to their orientation (normal vectors). Those triangles which have similar normal vectors can be considered to describe the same plane area 24 and therefore belong to the same group.

Thereafter, for each group of triangles a plane 32 can be reconstructed (e.g. by performing a fitting process of a plane to the corners of the triangles, i.e. the points of the mesh) that corresponds to a plane area 24 of the scan geometry 21. The reconstructed planes 32 can then be used to reconstruct intersection points 34 corresponding to corners 25 of the scan geometry 21. Three such reconstructed planes 32 can be used to determine one intersection point 34. Triangles (or corners of triangles) of the finite element description of the surface of a scan geometry 21, which correspond to parts of the surface that are located close (e.g. closer than 0.1 mm) to the edges or corners of a plane area 24, are preferably not taken into account in the plane 32 fitting procedure, because these triangles might be tilted or shifted up or down with respect to the corresponding plane area 24, which could result in a less precise fitting result. For example only the triangles or corners of triangles may be used which are located within circle around a mean location of triangles or corners of triangles of a group. The radius of the circle is chosen sufficiently small such as to ensure that only triangles or corners of triangles which are on the same plane 24 are taken into account for one plane fitting procedure. It is noted that even though a single triangle is sufficient to define/determine a plane 32 corresponding to a plane area 24 of a scan body 11, it is preferable to take the average over multiple triangles (e.g. more than 100, 200, or 500 and/or less than 1000 or 10000) for the definition of a plane 32 in order to increase the precision of this determination.

After the reconstruction of intersection points 34 and the association of the reconstructed intersection points 34 with physical corners 25, there is the possibility to compare the spatial positions of the reconstructed intersection points 34 with the expected spatial positions of points which, for instance, can be part of a digital model of a scan body. The latter comparison can be performed just as a consistency check, or it can be used for applying corrections to the position and orientation of a scan body 11 or an implant 12, respectively.

In case that the longitudinal axis of the scan body can be determined otherwise (e.g. from a global match which tries to fit the entire scan body into a scanned data set) this longitudinal axis can be used for verifying that the user has selected a triangle on the top plane area of the scan body by checking the position of the triangle with respect to its location along the longitudinal axis. If it is not almost on the most outward position along the longitudinal axis, an error message may be provided indicating that the user has not selected a triangle on the top plane area of the scan body.

In order to obtain a more detailed picture of the dental environment or a more complete virtual model, respectively, the scanning procedure can involve scanning of a scan body 11 within a dental environment from different points of view 14 and different perspectives (e.g. a top view and two side views), respectively. The information of multiple scans can be combined by identifying overlapping regions (e.g. of the scan body 11) and by merging information derived from individual scans. In this way, a basically complete three dimensional model can be created, which can be rotated and looked at from every thinkable point of view. Making use of combined data of different scans typically leads to more reconstructed straight intersection lines 33 and possibly also to more reconstructed intersection points 34 corresponding to physical corners 25. Hence, the number of determined corners 25' can be more than one, typically more than three, five or seven. The plurality of determined corners 25' can then be used to be fitted into a model of the scan body 11 or its corners 25 respectively, in order to determine the position and orientation of a corresponding dental implant 12.

It is noted that for the reconstruction of straight intersection lines 33 and of intersection points 34, it is not necessary that physical corners 25 or physical edges 26 are visible during the scanning procedure. For the reconstruction of plane 32, it is sufficient that at least three data points can be taken which lie inside one particular plane area 24. Therefore, the scanning and reconstruction procedure also works well if the data points 31 are not located closely to physical corners 25 or edges 26. Moreover, since no points on corners 25 or edges 26 are required for the determination of the position and the orientation of an implant 12, it is possible to take less points 31 during the scanning procedure, which allows the scanning to be performed faster. Further by reconstructing the planes data points can be taken into account that actually lie on the corresponding plane areas of the scan body. Trying to find corners or edges of the scan body is less precise since there may be only few data points which actually lie on such edges or corners. In summary, the determination of the position and orientation of a dental implant 12 of the present invention is more reliable and at the same time allows for a simpler scanning procedure.

The determined position and orientation of the implant can be used for modelling an abutment to be fixed on the implant or any other part to be fixed on the abutment or the implant such as a bridge, crown or the like. Also the insertion direction of the part to be fixed onto the implant or abutment can be determined from the information obtained.

The invention claimed is:

1. A scan body for determining a position and an orientation of a dental implant, the scan body comprising:
   a bottom end with means for connecting the scan body with the implant, wherein the scan body is connected directly to the implant or wherein the scan body is connected with the implant via an adaptor piece; and
   a top end having a scan geometry;
   wherein the scan geometry comprises a plurality of plane areas, each plane area having a plurality of sides and corners and each side having a length, and wherein the scan geometry comprises at least three types of plane areas having different orientation angles with respect to a longitudinal axis of the scan body,
   wherein the at least three types of plane areas include a top plane area and at least two different side plane areas, wherein the at least two different side plane areas are disposed at different orientation angles with respect to the longitudinal axis of the scan body, and at least one of the at least two different side plane areas extends continuously from the bottom end of the scan body to the top plane area, the side plane areas defining a limiting volume of cross-section that is narrower proximate the top plane area,
   wherein an orientation angle of at least one type of plane areas lies within a range of 30° to 60° with respect to the longitudinal axis,
   wherein the top plane area has a normal vector that is parallel to the longitudinal axis of the scan body,
   wherein the length of each side of one type of plane area is equal, or wherein the lengths of at least two sides of one type of plane area are different,
   such that from every possible point of view, located at a same level or above said scan geometry, there are at least three of said plane areas at least partly visible.

2. The scan body of claim 1, wherein the scan geometry is polyhedral, the scan geometry comprising a first corner and at least three additional corners, wherein the at least three additional corners define a plane, and wherein the first corner lies outside said plane.

3. The scan body of claim 1, the scan body further comprising a coding associating the scan body with a particular type of implant and/or with a particular type of adaptor piece.

4. The scan body of claim 3, wherein the coding is located such that the coding is visible from every possible point of view, where a possible point of view is located at the same level or sideways above said coding, where a point of view is located sideways above said coding in case an orientation of the scan body is such that the top end points up and the bottom end points down and the point of view is located at any position higher than the topmost end of the scan body.

5. The scan body of claim 3, wherein the coding comprises one or more ribs and/or channels and/or coloured rings.

6. The scan body of claim 1, wherein parts of the scan geometry are light reflective and/or parts of the scan geometry are non-light reflective.

7. The scan body of claim 1, wherein numbers of corners of at least two of the at least three types of plane areas are different.

* * * * *